United States Patent
Shimko et al.

(10) Patent No.: US 8,852,192 B2
(45) Date of Patent: Oct. 7, 2014

(54) METHOD AND APPARATUS FOR OSTEOCHONDRAL AUTOGRAFT TRANSPLANTATION

(75) Inventors: Daniel Shimko, Germantown, TN (US); Jeetendra Bharadwaj, Memphis, TN (US); Keith Matthew Kinnane, Bartlett, TN (US); Jeffrey H. Nycz, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2089 days.

(21) Appl. No.: 11/559,250

(22) Filed: Nov. 13, 2006

(65) Prior Publication Data

US 2008/0114368 A1 May 15, 2008

(51) Int. Cl.
| | |
|---|---|
| *A61B 17/56* | (2006.01) |
| *A61B 17/17* | (2006.01) |
| *A61B 17/16* | (2006.01) |
| *A61B 19/00* | (2006.01) |
| *A61B 17/00* | (2006.01) |

(52) U.S. Cl.
CPC .............. *A61B 17/1635* (2013.01); *A61B 17/17* (2013.01); *A61B 19/2203* (2013.01); *A61B 17/1703* (2013.01); *A61B 17/1764* (2013.01); *A61B 2017/00969* (2013.01); *A61B 17/1675* (2013.01)
USPC .............. 606/86 R; 606/96; 33/25.1; 409/124

(58) Field of Classification Search
USPC ............ 33/23.01, 23.05, 23.07, 23.08, 23.11, 33/25.1, 25.2; 128/898; 358/424, 478; 409/64–111, 124–132; 606/86 R, 96, 606/167, 170, 180; 623/915, 919
See application file for complete search history.

(56) References Cited

U.S. PATENT DOCUMENTS

| | | | | |
|---|---|---|---|---|
| 361,131 | A * | 4/1887 | Carlinet | 409/86 |
| 1,923,208 | A * | 8/1933 | Howey | 358/474 |
| 3,100,344 | A * | 8/1963 | Sharp | 433/76 |
| 3,858,324 | A * | 1/1975 | Padowicz | 33/25.1 |
| 3,929,462 | A * | 12/1975 | Karmin | 434/162 |
| 4,176,585 | A * | 12/1979 | Anderson | 409/125 |
| 4,182,312 | A * | 1/1980 | Mushabac | 433/68 |
| 4,215,960 | A * | 8/1980 | Tsuzuki | 409/121 |

(Continued)

FOREIGN PATENT DOCUMENTS

| | | | | |
|---|---|---|---|---|
| WO | WO 94/24933 | 11/1994 | | |
| WO | WO 96/11624 | 4/1996 | | |
| WO | WO 2006067630 A2 * | 6/2006 | ............. | A61C 13/00 |

OTHER PUBLICATIONS

U.S. Appl. No. 11/508,349, filed Aug. 23, 2006, Bharadwaj.

(Continued)

*Primary Examiner* — Nicholas Woodall
*Assistant Examiner* — Larry E Waggle, Jr.
(74) *Attorney, Agent, or Firm* — Sorell Lenna & Schmidt LLP

(57) ABSTRACT

A surgical procedure for preparing a graft for insertion in an opening in a human body, according to which a mold is formed in the opening and transferred from the opening to a position adjacent a stylus. A contour of the mold is traced with the stylus; and the tracing movement of the stylus is transferred to corresponding movement of a cutting member so that the cutting member cuts the same contour in the graft.

15 Claims, 2 Drawing Sheets

(56) References Cited

U.S. PATENT DOCUMENTS

| | | | |
|---|---|---|---|
| 4,317,644 A * | 3/1982 | Hosoi | 409/98 |
| 4,403,961 A * | 9/1983 | Gurney | 433/213 |
| 4,645,347 A * | 2/1987 | Rioux | 356/609 |
| 4,961,154 A * | 10/1990 | Pomerantz et al. | 345/419 |
| 5,135,393 A * | 8/1992 | Eidenbenz et al. | 433/53 |
| 5,383,454 A | 1/1995 | Bucholz | |
| 5,741,215 A * | 4/1998 | D'Urso | 600/407 |
| 5,782,915 A | 7/1998 | Stone | |
| 5,851,183 A | 12/1998 | Bucholz | |
| 5,865,849 A | 2/1999 | Stone | |
| 5,871,445 A | 2/1999 | Bucholz | |
| 5,891,034 A | 4/1999 | Bucholz | |
| 5,913,900 A | 6/1999 | Stone | |
| 5,919,196 A | 7/1999 | Bobic et al. | |
| 5,921,987 A | 7/1999 | Stone | |
| 5,964,805 A | 10/1999 | Stone | |
| 6,007,496 A | 12/1999 | Brannon | |
| D420,132 S | 2/2000 | Bucholz et al. | |
| 6,021,343 A | 2/2000 | Foley et al. | |
| 6,027,743 A | 2/2000 | Khouri et al. | |
| D422,706 S | 4/2000 | Bucholz et al. | |
| 6,093,204 A | 7/2000 | Stone | |
| 6,110,209 A | 8/2000 | Stone | |
| 6,110,482 A | 8/2000 | Khouri et al. | |
| 6,118,845 A | 9/2000 | Simon et al. | |
| 6,167,145 A | 12/2000 | Foley et al. | |
| 6,190,395 B1 | 2/2001 | Williams | |
| 6,226,548 B1 | 5/2001 | Foley et al. | |
| 6,235,038 B1 | 5/2001 | Hunter et al. | |
| 6,236,875 B1 | 5/2001 | Bucholz et al. | |
| 6,253,210 B1 | 6/2001 | Smith et al. | |
| 6,306,142 B1 | 10/2001 | Johanson et al. | |
| 6,340,363 B1 | 1/2002 | Bolger et al. | |
| 6,348,058 B1 | 2/2002 | Melkent et al. | |
| 6,375,658 B1 | 4/2002 | Hangody et al. | |
| 6,379,302 B1 | 4/2002 | Kessman et al. | |
| 6,381,485 B1 | 4/2002 | Hunter et al. | |
| 6,395,011 B1 | 5/2002 | Johanson et al. | |
| 6,402,762 B2 | 6/2002 | Hunter et al. | |
| 6,434,415 B1 | 8/2002 | Foley et al. | |
| 6,434,507 B1 | 8/2002 | Clayton et al. | |
| 6,440,141 B1 | 8/2002 | Philippon | |
| 6,470,207 B1 | 10/2002 | Simon et al. | |
| 6,474,341 B1 | 11/2002 | Hunter et al. | |
| 6,488,033 B1 | 12/2002 | Cerundolo | |
| 6,490,467 B1 | 12/2002 | Bucholz et al. | |
| 6,491,699 B1 | 12/2002 | Henderson et al. | |
| 6,535,756 B1 | 3/2003 | Simon et al. | |
| 6,540,668 B1 | 4/2003 | Schulz et al. | |
| 6,553,152 B1 | 4/2003 | Miller et al. | |
| 6,592,588 B1 | 7/2003 | Bobic et al. | |
| 6,636,757 B1 | 10/2003 | Jascob et al. | |
| 6,669,635 B2 | 12/2003 | Kessman et al. | |
| 6,708,184 B2 | 3/2004 | Smith et al. | |
| 6,725,080 B2 | 4/2004 | Melkent et al. | |
| 6,754,374 B1 | 6/2004 | Miller et al. | |
| 6,767,354 B2 | 7/2004 | Johanson et al. | |
| 6,796,988 B2 | 9/2004 | Melkent et al. | |
| 6,852,114 B2 | 2/2005 | Cerundolo | |
| 6,892,090 B2 | 5/2005 | Verard et al. | |
| 6,920,347 B2 | 7/2005 | Simon et al. | |
| 6,932,842 B1 * | 8/2005 | Litschko et al. | 623/16.11 |
| 6,978,166 B2 | 12/2005 | Foley et al. | |
| 7,007,699 B2 | 3/2006 | Martinelli et al. | |
| RE39,133 E | 6/2006 | Clayton et al. | |
| 2004/0034437 A1 | 2/2004 | Schmieding | |
| 2004/0039400 A1 | 2/2004 | Schmieding et al. | |
| 2004/0059425 A1 | 3/2004 | Schmieding | |
| 2004/0176771 A1 | 9/2004 | Schmieding | |
| 2004/0193154 A1 | 9/2004 | Leatherbury et al. | |
| 2004/0230303 A1 | 11/2004 | Gomes | |
| 2004/0236424 A1 * | 11/2004 | Berez et al. | 623/14.12 |
| 2005/0101962 A1 | 5/2005 | Schwenke et al. | |
| 2005/0222687 A1 | 10/2005 | Vunjak-Novakovic et al. | |
| 2006/0060209 A1 | 3/2006 | Shepard | |
| 2007/0172506 A1 * | 7/2007 | Nycz et al. | 424/422 |
| 2007/0237595 A1 * | 10/2007 | Steger | 409/132 |

OTHER PUBLICATIONS

U.S. Appl. No. 11/514,433, filed Sep. 1, 2006, Nycz, et al.
U.S. Appl. No. 11/551,979, filed Oct. 23, 2006, Bharadwaj.
U.S. Appl. No. 11/559,013, filed Nov. 13, 2006, Anderson, et al.

* cited by examiner

METHOD AND APPARATUS FOR OSTEOCHONDRAL AUTOGRAFT TRANSPLANTATION

BACKGROUND

This invention relates to an improved osteochondral autograft transplantation method and apparatus, and more particularly, to such a procedure and apparatus in which a graft is prepared for a recipient opening.

The human knee consists of three bones—a femur, a tibia, and a patella—that are held in place by various ligaments. The corresponding condyles of the femur and the tibia form a hinge joint, and the patella protects the joint. Portions of the condyles, as well as the underside of the patella, are covered with an articular cartilage, which allow the femur and the tibia to smoothly glide against each other without causing damage.

The articular cartilage often tears, usually due to traumatic injury (often seen in athletes) and degenerative processes (seen in older patients). This tearing does not heal well due to the lack of nerves, blood vessels and lymphatic systems; and the resultant knee pain, swelling, and limited motion of the bone(s) must be addressed.

Damaged adult cartilages have historically been treated by a variety of surgical interventions including lavage, arthroscopic debridement, and repair stimulation, all of which provide less than optimum results.

Another known treatment involves removal and replacement of the damaged cartilage with a prosthetic device. However, prostheses have largely been unsuccessful since they are deficient in the elastic, and therefore in the shock-absorbing, properties characteristic of the cartilage. Moreover, prostheses have not proven able to withstand the forces inherent to routine knee joint function.

In an attempt to overcome the problems associated with the above techniques, osteochondral autograft transplantation, also known as "mosaicplasty" has been used to repair articular cartilages. This procedure involves removing injured tissue from the damaged area and drilling one or more openings in the underlying bone. A graft, or plug, consisting of healthy cartilage overlying bone, is obtained from another area of the patient, typically from a lower weight-bearing region of the joint under repair, or from a donor patient, and is implanted in each opening. It is extremely important that each plug fit in its opening in a precise manner, and an embodiment of the present invention involves a technique for advancing the art in this respect.

DETAILED DESCRIPTION

Figure 1:
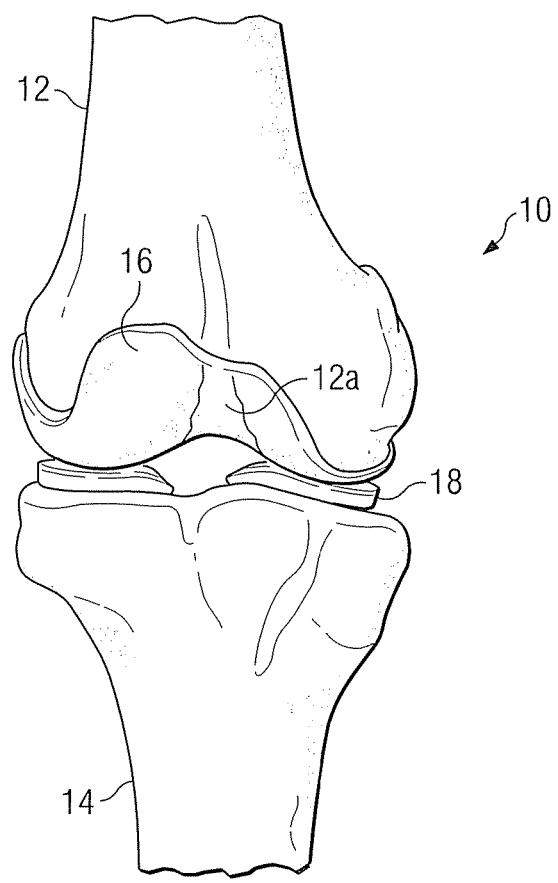
FIG. 1 is an elevational view of a human knee with certain parts removed in the interest of clarity.

Referring to FIG. 1 of the drawing, the reference numeral 10 refers, in general, to a knee area of a human including a femur 12 and a tibia 14 whose respective condyles are in close proximity. A cartilage 16 extends over a portion of the condyle of the femur 12, and a meniscus 18 extends between the cartilage and the tibia 14. The patella, as well as the tendons, ligaments, and quadriceps that also form part of the knee, are not shown in the interest of clarity.

Figure 2A:
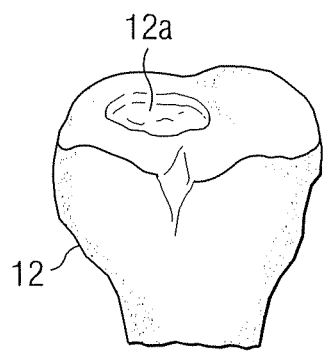
FIGS. 2A and 2B are isometric views depicting the femur of the knee of FIG. 1 and illustrating two steps in the procedure according to an embodiment of the invention.

Referring to FIG. 2A, which depicts the femur 12 of FIG. 1 in an inverted position, it will be assumed that a portion of the cartilage 16 extending over the condyle of the femur 12 has been damaged and resected by the surgeon, or has worn away, leaving a damaged area, or defect 12a. It will be also assumed that the surgeon has surgically removed areas of the bone below the damaged cartilage at the defect 12a so as to form an opening that is suited to receive a plug, or graft. The latter procedure can involve drilling a hole in the underlying bone to a predetermined depth, as shown.

A graft is harvested from another area of the patient/recipient, such as an undamaged non-load bearing area of the femur or tibia, or from a corresponding area of a donor, in accordance with known techniques.

Techniques for preparing the defect and/or harvesting the graft are disclosed with more specificity in pending U.S. patent application Ser. No. 11/340,024, filed Jan. 26, 2006; Ser. No. 11/338,926, filed Jan. 25, 2006; Ser. No. 11/339,194, filed Jan. 25, 2006; Ser. No. 11/317,985, filed Dec. 23, 2005; Ser. No. 11/340,884, filed Jan. 27, 2006; Ser. No. 11/343,156, filed Jan. 30, 2006; and Ser. No. 11/339,694, filed Jan. 25, 2006, the disclosures of which are hereby incorporated by reference.

Figure 2B:
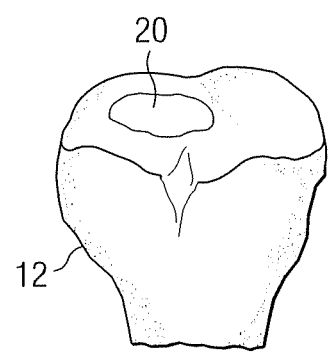
Figure 3:
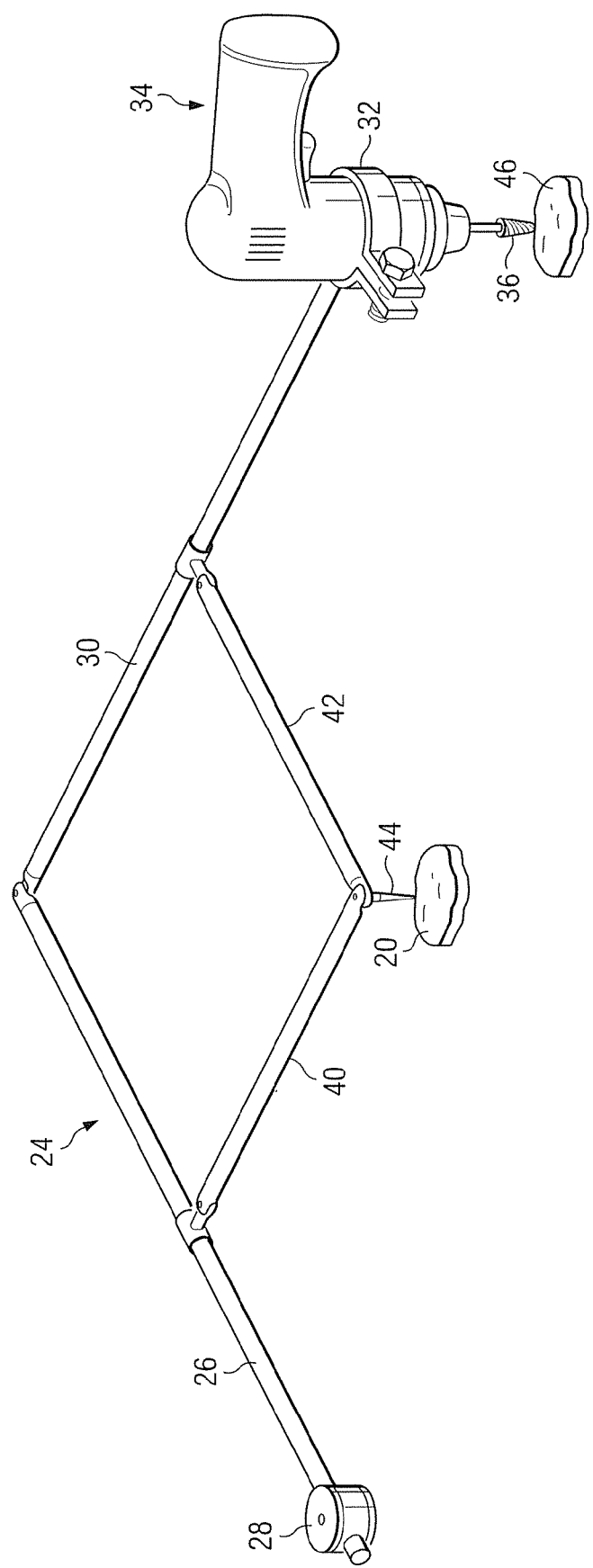
FIG. 3 depicts a copy mill apparatus according to an embodiment of the invention.

This graft only generally corresponds to the above-mentioned opening in the defect 12a in size and shape, and FIGS. 2B and 3 depict a system that enables the graft to precisely fit in the opening.

To this end, and with reference to FIG. 2B, which depicts the femur of FIG. 2A, a soft material such as putty, or the like, is placed in the opening in the defect 12a and allowed to harden to form a mold 20. Since this type of material is conventional, it will not be described in detail. The hardened mold 20 is then removed from the defect 12a and transferred to a copy-mill apparatus shown, in general, by the reference numeral 24 in FIG. 3.

The apparatus 24 consists of an arm 26 anchored at one end portion by a fixed base 28, and pivotally mounted at its other end to an arm 30. The arms 26 and 30 extend generally at right angles to each other, and the other end of the arm 30 is fixed to an adjustable mounting ring 32. An electric drill 34 is secured in the ring 32 and includes a grinding bit 36 that is rotated by the drill.

The respective ends of two additional arms 40 and 42 are affixed to the arms 26 and 30, respectively, in any conventional manner. The arms 40 and 42 are shorter than the arms 26 and 30, and are connected to the arms at an area between the ends of the latter arms. The arms 40 and 42 extend generally perpendicularly to the arms 26 and 30, respectively, and the other ends of the arms 40 and 42 are pivotally connected to each other. A stylus 44 is mounted at or near the pivot point between the latter ends of the arms 40 and 42.

A graft, described above and referred to by the reference numeral 46 in FIG. 3, is placed near the bit 36, and the mold 20 is placed near the stylus 44. The electric drill 34 is activated and the surgeon manually manipulates the stylus 44 so that it traces the contour of the mold 20. The articulation of the arms 26 and 30 and the arms 40 and 42 causes the movement of the stylus 44 to be transferred to corresponding movement of the drill 34 and the bit 36. Thus, the bit 36 grinds, or cuts, the graft 46 in a contour that corresponds to the contour of the mold 20.

It is understood that the stylus 44 can trace other contours on other surfaces of the mold 20, in which case the bit 36 would be oriented relative to the graft 46 so that the same contour is cut in the graft.

According to an alternate embodiment, instead of using a mold, the surgeon could use a conventional computer tomography scan, or a computer axial tomography scan, to develop a three dimensional model of the defect 12a. According to these procedures the instrument takes a series of X-Rays along a fixed axis on which the patient is moved. Computer software is then used to reconstruct the plane x-rays into a three dimensional model of the tissues in the body. Computer software could then be used to create a negative three dimensional model of the defect void.

Alternately, magnetic resonance imaging or laser scanning could be used to develop the three dimensional model. Further, the model could be reproduced using computer controlled instruments for the manufacture of three dimensional products, such as a rapid prototype device, a three dimensional printer or a stereolithograph, for example. These instruments use a variety of materials and methods to generate three dimensional models from computerized data sets. Still further, the model can be formed using a free hand instrument that is bounded in three dimensional space by a robot using the data obtained from the scan of the defect region.

Since the techniques discussed in the previous two paragraphs are conventional, they will not be described in detail.

After the model is formed in accordance with one of the above procedures, it could then be placed into the copy mill in the same manner as the mold 20 and could also be used to shape a graft according to the procedure disclosed above.

A graft formed in accordance with each of the above embodiments can then be implanted in the opening in the defect 12a (FIG. 2A), with the assurance that it will fit in a precise manner. In the latter context, examples of tools for retaining a graft and implanting it in an opening are well disclosed in U.S. patent application Ser. No. 10/792,780, filed on Mar. 5, 2004 (now U.S. publication no. 2004/0176771, published Sep. 9, 2004); U.S. patent application Ser. No. 10/785,388, filed on Feb. 23, 2004 (now U.S. application publication no. 2004/0193154, published Sep. 30, 2004); U.S. patent application Ser. No. 10/984,497, filed Nov. 9, 2004; (now U.S. application publication no. 2005/0101962, published May 12, 2005); U.S. patent application Ser. No. 10/815,778, filed Apr. 2, 2004 (now U.S. application publication no. 2005/0222687, published Oct. 6, 2005); U.S. patent application Ser. No. 08/885,752, filed Jun. 30, 1997 (now U.S. Pat. No. 5,919,196 granted Jul. 6, 1999); U.S. patent application Ser. No. 08/797,973, filed Feb. 12, 1997 (now U.S. Pat. No. 5,921,987 granted Jul. 13, 1999); U.S. patent application Ser. No. 08/908,685, filed Aug. 7, 1997 (now U.S. Pat. No. 5,964,805, granted Oct. 12, 1999); U.S. patent application Ser. No. 08/774,799 filed Dec. 30, 1996 (now U.S. Pat. No. 6,007,496); U.S. patent application Ser. No. 09/187,283, filed on Nov. 5, 1998 (now U.S. Pat. No. 6,110,209, granted Aug. 29, 2000); U.S. patent application Ser. No. 09/425,337, filed Oct. 22, 1999 (now U.S. Pat. No. 6,306,142, granted Oct. 23, 2001); U.S. patent application Ser. No. 09/559,532, filed Apr. 28, 2000 (now U.S. Pat. No. 6,375,658, granted Apr. 23, 2002); U.S. patent application Ser. No. 09/118,680, filed Jul. 17, 1998 (now U.S. Pat. No. 6,395,011, granted May 28, 2002); U.S. patent application Ser. No. 09/624,689, filed Jul. 24, 2000 (now U.S. Pat. No. 6,440,141, granted Aug. 27, 2002); U.S. patent application Ser. No. 09/571,363, filed May 15, 2000 (now U.S. Pat. No. 6,488,033, granted Dec. 3, 2002); U.S. patent application Ser. No. 09/243,880, filed Feb. 3, 1999 (now U.S. Pat. No. 6,592,588, granted Jul. 15, 2003); U.S. patent application Ser. No. 10/004,388, filed Oct. 23, 2001 (now U.S. Pat. No. 6,767,354, granted Jul. 27, 2004); U.S. patent application Ser. No. 10/084,490, filed Feb. 28, 2002 (now U.S. Pat. No. 6,852,114, granted Feb. 8, 2005); U.S. patent application Ser. No. 10/665,152, filed on Sep. 22, 2003 (now U.S. publication no. 2004/0059425, published Mar. 25, 2004); U.S. patent application Ser. No. 10/638,489, filed on Aug. 12, 2003 (now U.S. publication no. 2004/0034437, published Feb. 19, 2004); U.S. patent application Ser. No. 10/443,893, filed on May 23, 2003 (now U.S. publication no. 2004/0039400, published Feb. 26, 2004); U.S. patent application Ser. No. 10/947,217, filed on Sep. 23, 2004 (now U.S. publication no. 2006/0060209, published Mar. 23, 2006). The disclosures of each of these patent applications and publications are incorporated herein by reference.

Variations (1) The present invention procedure is not limited to preparing a graft for implantation in the knee, but is equally applicable to other parts of the body.
(2) More than one opening, of the type described above, can be formed at or near the defect.
(3) A mechanism other than the ring 32 can be used to mount the drill 34 to the rod 30.
(4) The graft could take the form of a synthetic or natural material/scaffold used for resurfacing the defect.

Those skilled in the art will readily appreciate that many other variations and modifications of the embodiment described above can be made without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A surgical procedure for preparing a harvested graft for implantation in an opening in a human body, the procedure comprising:
    forming a mold in the opening;
    transferring the mold from the opening to a position adjacent a stylus; tracing a contour of the mold with the stylus;
    providing the harvested graft having a size and shape that generally corresponds to the opening; and
    transferring the tracing movement of the stylus to corresponding movement of a cutting member so that the cutting member cuts the same contour in the graft, wherein the cut graft precisely fits the opening.

2. The procedure of claim 1 wherein the opening is formed in a defect in a femur, and further comprising surgically removing areas of a cartilage from the defect before the opening is formed.

3. The procedure of claim 1 further comprising tracing at least one other contour of the mold with the stylus; and transferring the latter tracing movement of the stylus to corresponding movement of the cutting member so that the cutting member cuts the other contour in the graft.

4. The procedure of claim 1 wherein the cutting member is a grinding bit attached to an electric drill for rotating the bit.

5. The procedure of claim 1 wherein the step of transferring comprises connecting the stylus and the cutting member to an assembly of articulating arms so that movement of the stylus causes corresponding movement of the cutting member.

6. The procedure of claim 1 further comprising harvesting a graft from a non-load bearing area of a femur or tibia to produce the harvested graft.

7. The procedure of claim 1 wherein forming the mold comprises placing a putty into the opening and allowing the putty to harden to form the mold.

8. A surgical procedure for preparing a harvested graft for implantation in a defect, the procedure comprising:
    scanning the defect region;
    forming a model of the defect;
    placing the model into a copy mill;
    manually manipulating a stylus to trace tracing a contour of the model mold with a stylus in the copy mill;
    providing the harvested graft having a size and shape that generally corresponds to the opening; and
    transferring the tracing movement of the stylus to corresponding movement of a cutting member so that the cutting member cuts the same contour in the graft, wherein the cut graft precisely fits the opening.

9. The procedure of claim 8, wherein a computer tomography scan is used in the step of scanning.

10. The procedure of claim 8, wherein magnetic resonance imaging is used in the step of scanning.

11. The procedure of claim 8, wherein a laser scanner is used in the step of scanning.

12. The procedure of claim 8, wherein a rapid prototype device is used in the step of forming.

13. The procedure of claim 8, wherein a three dimensional printer is used in the step of forming.

14. The procedure of claim 8, wherein the model is formed by a free hand instrument that is bounded in three dimensional spaces by a robot using the data obtained from the step of scanning.

15. The procedure of claim 8 wherein the step of forming comprises creating a negative model of the defect, and reproducing the negative model.

* * * * *